United States Patent
Jamerson et al.

(10) Patent No.: US 9,597,364 B2
(45) Date of Patent: Mar. 21, 2017

(54) TREATMENT OF WITHDRAWAL SYMPTOMS TO AID IN NICOTINE USE CESSATION WITH PASSIFLORA INCARNATA

(71) Applicant: Campbell University, Buies Creek, NC (US)

(72) Inventors: Brenda Diane Jamerson, Buies Creek, NC (US); Christopher Scott Breivogel, Buies Creek, NC (US)

(73) Assignee: Campbell University, Buies Creek, NC (US)

( * ) Notice: Subject to any disclaimer, the term of this patent is extended or adjusted under 35 U.S.C. 154(b) by 0 days.

(21) Appl. No.: 15/165,661

(22) Filed: May 26, 2016

(65) Prior Publication Data

US 2016/0271194 A1 Sep. 22, 2016

Related U.S. Application Data

(63) Continuation of application No. 14/256,600, filed as application No. PCT/US2012/060802 on Oct. 18, 2012, now Pat. No. 9,375,455.

(60) Provisional application No. 61/548,245, filed on Oct. 18, 2011.

(51) Int. Cl.
*A61K 36/185* (2006.01)
*A61K 45/06* (2006.01)

(52) U.S. Cl.
CPC ............ *A61K 36/185* (2013.01); *A61K 45/06* (2013.01)

(58) Field of Classification Search
None
See application file for complete search history.

(56) References Cited

U.S. PATENT DOCUMENTS

| 6,645,470 B1 | 11/2003 | Reynolds |
| 2001/0036486 A1 | 11/2001 | Rosenthal et al. |
| 2005/0100513 A1 | 5/2005 | Watkins et al. |
| 2005/0227998 A1 | 10/2005 | Voelker |

FOREIGN PATENT DOCUMENTS

| WO | 02066041 A1 | 8/2002 |
| WO | 2006/097447 A1 | 9/2006 |

OTHER PUBLICATIONS

Yarnell, Eric "*Passiflora incarnate* L (passionflower), Passifloraceae and related species", Bastyr University, Department of Botanical Medicine, 2007 [online] Retrieved from the internet: <URL:http://www.aaronsworld.com/Bastyr/Class%20Notes/Bot%20Med/Bot%20Med%20V/Passiflora_incarnata.pdf>.

Search Report and Written Opinion Corresponding PCT Application No. 2012/060802, Mailed Feb. 14, 2013.

Dhawan et al., "Nicotine reversal effects of the benzoflavone moiety from Passiflora incarnata Linneaus in mice", Adiction Biology, 7, 435-551, 2002.

Yarnell et al. "Botanical Remedies for Nicotine Addiction", adapted from Abascale K. Botanical remedies for nicotine addiction, Natural Pharmacy, 5(9):1, 11-13, 2001, Atlernative & Complementary Therapies, pp. 337-340, Dec. 2001.

*Primary Examiner* — Susan Hoffman
(74) *Attorney, Agent, or Firm* — James G. Passé; Passé Intellectual Property, LLC

(57) ABSTRACT

The present invention relates to the treatment of withdrawal and craving symptoms as an aid in smoking cessation by administration of one or more dosages of a medication containing *Passiflora incarnata*.

1 Claim, 3 Drawing Sheets

TREATMENT OF WITHDRAWAL SYMPTOMS TO AID IN NICOTINE USE CESSATION WITH PASSIFLORA INCARNATA

This application is a Continuation of U.S. non-provisional application Ser. No. 14/256,600 filed on Apr. 18, 2014, U.S. Pat. No. 9,375,455, which was a '371 National Stage filing of PCT/US2012/060802 filed on Oct. 18, 2012, which claims priority of US provisional application No. 61/548,245 filed on Oct. 18, 2011, and all are included herein in their entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to a method of treating an individual during nicotine withdrawal. In particular, the present invention relates to treating an individual who is addicted to nicotine with *Passiflora incarnata*, or an extract thereof, to prevent withdrawal and craving symptoms during nicotine cessation to aid in smoking cessation.

2. Description of Related Art

Tobacco is the single greatest cause of disease and premature death today in America and is responsible for more than 440,000 deaths each year. Despite the morbidity, mortality, and cost to smoking, nearly 21% of all adult Americans continue to smoke.

Nicotine, the active ingredient responsible for the addictive nature of cigarette smoking and use of other nicotine containing products such as snuff, chew tobacco, and the like, exerts excitatory and inhibitory pharmacologic effects which account for its stimulating yet calming effects. The compound binds to central nicotinic receptors causing release of the neurotransmitter dopamine in the mesolimbic area, the corpus striatum, and the frontal cortex. An increase in dopamine levels in the nucleus accumbens has been shown related to the addictive properties of nicotine.

Dopaminergic projection to the nucleus accumbens arises from neurons in the central tegmental area (VTA). Dopamine release from VTA projections is related to both excitatory and inhibitory inputs. In rat studies, it has been demonstrated that the inhibitory input to the VTA neurons are primarily GABAergic. Therefore, GABA agonists which have an action to inhibit neuronal outflow via this pathway may theoretically modulate dopamine release.

Nicotine replacement therapy (NRT), bupropion and varenicline are currently FDA approved as smoking cessation aids in the United States.

Extracts of passion flower have been used in traditional and herbal medicines for anxiety, insomnia, and seizures, but controlled clinical studies of passion flower extract for these indications are limited. Passion flower extract has been examined in double blind studies and shown to treat generalized anxiety disorder similar to oxazepram, to help patients through opiate withdrawal, and to help alleviate presurgical anxiety. In laboratory rodents, passion flower extract or single chemical constituents of passion flower have been shown to be sedative, anxiolytic and anticonvulsant. Moreover, numerous studies in laboratory rodents have demonstrated that whole extracts or a specific benzoflavone moiety from passion flower are anxiolytic, antitussive and aphrodisiac and may reduce certain kinds of drug dependence other than nicotine. They have shown that the benzoflavone drug, given together with the addictive agent during the induction of dependence, reduced the symptoms of antagonist-precipitated withdrawal to morphine, alcohol, nicotine, diazepam and Δ9-tetrahydrocannabinol.

As demonstrated in previous studies, an acute injection of nicotine to rats results in increased locomotion, and daily injections result in sensitization to this effect. This hyperlocomotion effect is used as a model of nicotine addiction or withdrawal and agents that block the expression of this hyperlocomotion are considered useful in treating the signs of withdrawal from nicotine in humans.

BRIEF SUMMARY OF THE INVENTION

The present invention relates to the discovery that an administration of *Passiflora incarnata* as whole plant or an extract, such as an alcohol extract in a therapeutically effective amount would reduce the severity of the symptoms of nicotine withdrawal during smoking cessation.

Accordingly, one embodiment of the invention comprises a method for reducing nicotine withdrawal symptoms associated with nicotine product cessation in a patient in need thereof comprising administering to the patient a composition comprising *Passiflora incarnate*, or an extract thereof, in a pharmaceutically acceptable carrier in a therapeutically effective amount.

DETAILED DESCRIPTION OF THE INVENTION

Figure 1:
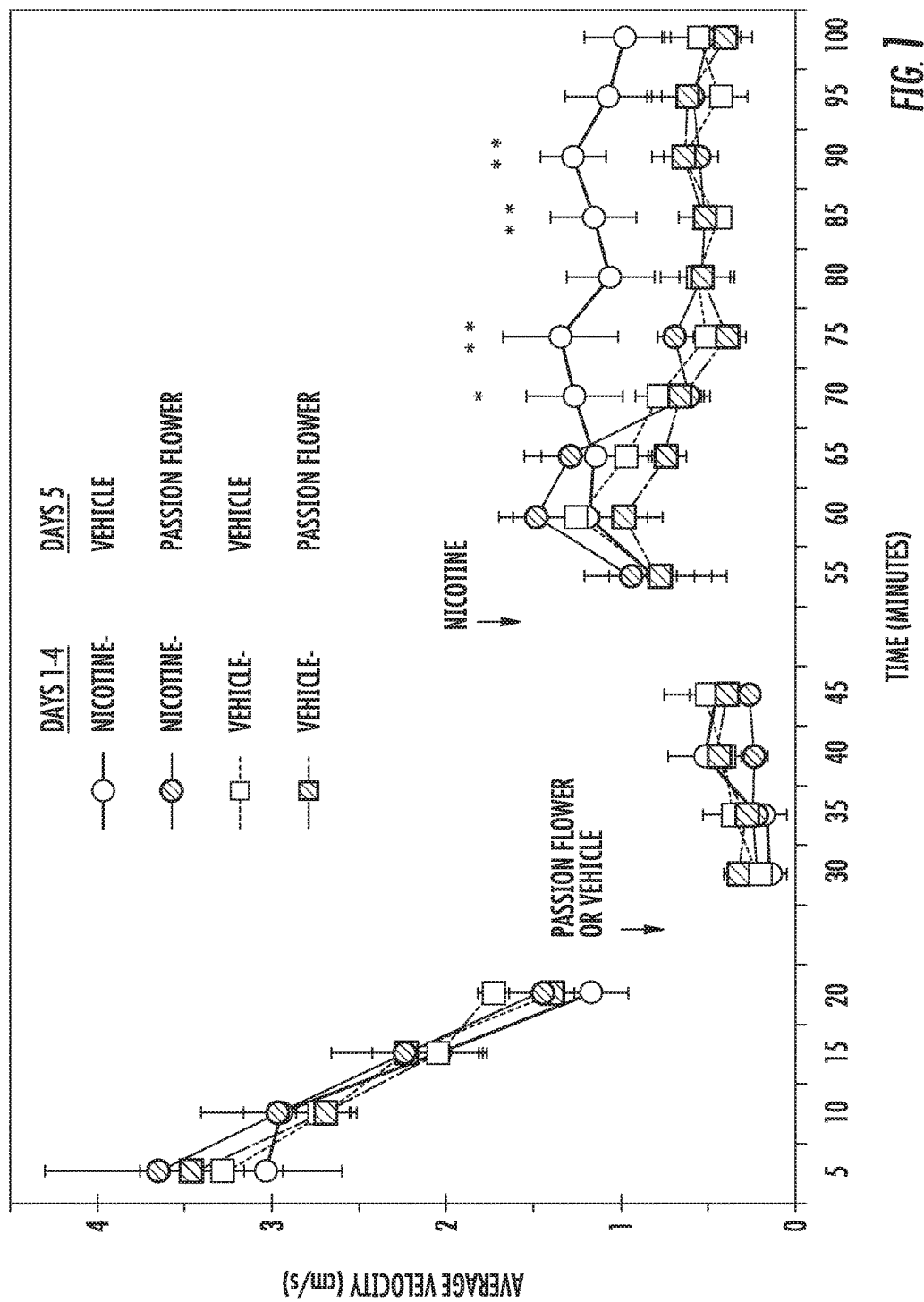
FIGS. 1-3 show the results of treatment of nicotine habituation with Passion flower treatment.

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The terms "about" and "essentially" mean ±10 percent.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

All patents, patent applications and literature cited in this description are incorporated herein by reference in their entirety. In the case of inconsistencies, the present disclosure including definitions will prevail.

As used herein the phrase "*Passiflora incarnata*" refers to the plant in any of its forms including the whole flower, the dried flower, and aqueous solutions, extracts and tinctures including extracts of alcohol and the like. Ethanol extracts for example in 25% ethanol are within the scope of the extracts of the present invention. Exact dosaging will depend on the particular strain of plant, the route of administration, the formulation used to administer the composition, and the like. One skilled in the art with the knowledge of the present invention that *Passiflora incarnata* can be used to treat nicotine withdrawal and aid in nicotine product cessation, can easily and without undue experimentation determine the right amount of composition to administer to an individual in light of the disclosure herein including the definition of a therapeutic amount.

In addition, pharmaceutically acceptable carriers may be used in the compositions of the present invention. The term "pharmaceutically acceptable carrier" refers to a carrier that may be administered to a patient, together with *Passiflora incarnata*, and which does not destroy the pharmacological activity thereof and is nontoxic when administered in doses sufficient to deliver a therapeutic amount of the compositions of the present invention.

Non-limiting exemplary examples of pharmaceutically acceptable carriers include, ion exchangers, alumina, aluminum stearate, lecithin, self-emulsifying drug delivery systems (SEDDS) such as d alpha-tocopherol polyethyl-enegly-col 1000 succinate, or other similar polymeric delivery matrices or systems, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-.beta.-cyclodextrins, or other solublized derivatives may also be advantageously used to enhance delivery of therapeutically-effective *Passiflora incarnata*.

The compositions of the present invention may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like.

As used herein the phrase "nicotine product cessation" refers to cessation of the use of products that contain nicotine. Smoking cessation, such as use of cigarettes, cigars, pipes, and the like, as well as chew tobacco, snuff, and the like are all within this definition. The intention is the cessation of products that an individual is addicted to or otherwise is trying to quit which contains nicotine supporting a nicotine habit. As used herein where the phrase "smoking cessation" is used it also encompasses cessation of any nicotine containing product.

As used herein, "therapeutically effective amount" or "therapeutically effective dose" means a nontoxic but sufficient amount of an active agent to provide the desired therapeutic effect (i.e., minimizing nicotine withdrawal symptoms). It will be understood, however, that the total usage (daily or otherwise) of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. The dosage ranges for the present invention are all well above the current minimums used in the art. Starting dosages where the dosage is tapered upward would also start at a much higher than the minimal amounts than occur in present preparations. A minimum dosage would be in the range of 2 gm per day and may range up to 60 gm or more as needed for the individual. The pharmaceutical compositions of the present invention may be administered orally, intracisternally, intravaginally, intraperitoneally, topically (as by powders, ointments, drops or transdermal patch), rectally, or bucally. In one embodiment, the pharmaceutical compositions of the present invention comprising a *Passiflora incarnata* medication are administered orally.

The pharmaceutical compositions of the present invention may be in a form suitable for transdermal administration. By "transdermal drug delivery" is meant administration of a drug to the skin surface of an individual so that the drug passes through the skin tissue and into the individual's blood stream, thereby producing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The pharmaceutical compositions of the present invention may be in a form suitable for oral use, for example, as tablets, lozenges, aqueous or oily suspensions, dispersible powders or granules, emulsions, hard or soft capsules, syrups or elixirs. Compositions intended for oral use may be prepared according to any method known to the art for the manufacturer of pharmaceutical compositions and such compositions may contain one or more agents such as, for example, sweetening agents, flavoring agents, coloring agents and the like, in order to provide a pharmaceutically elegant and palatable preparation.

Tablets contain the active ingredients in admixture with nontoxic pharmaceutically acceptable excipients which are suitable for manufacture of tablets. These excipients may be inert diluents, for example, calcium carbonate, sodium carbonate, lactose, calcium phosphate or sodium phosphate; granulating and disintegrating agents, for example, alginic acid, maize starch or; binding agents, for example, acacia, gelatin or starch, and lubricating agents, for example, magnesium stearate or stearic acid. The tablets may be uncoated or they may be coated by known techniques to delay disintegration and absorption in the gastro-intestinal tract and thereby provide an even longer sustained action over a period of time. The tablets may be chewable or non-chewable and designed to desired weight, potency and hardness through well known skills in the pharmaceutical arts.

Formulations for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with a suitable oil medium, for example, arachis oil, liquid paraffin or olive oil.

Formulations for oral use may also be presented as lozenges wherein the active ingredients are mixed into a hard candy composition. Suitable hard candy compositions can be made from varying, but highly concentrated, sucrose solutions including corn syrup as a second essential ingredient. Other known hard candy compositions may utilize any suitable good tasting, sweet excipient other than sucrose.

Aqueous suspensions contain the active ingredients in admixture with excipients suitable for the manufacture of aqueous suspensions. Such excipients or combinations thereof may be suitable suspending agents, for example, alginates, carboxymethylcellulose, carboxypolymethylene, carrageenan, colloidal silicon dioxide, corn starch, flowable starch, gelatin, guar gum, gum acacia, gum tragacanth, hydroxypropylcellulose, hydroxypropylmethylcellulose, maltodextrin, methylcellulose, microcrystalline cellulose, pectin, polyethylene glycol 800, polyvinyl alcohol, polyvinylpyrrolidone, sodium alginate, sodium carboxymethyl cellulose or xanthane gum; dispersing or wetting agents may be any suitable naturally occurring phosphatides, for example, lecithin, or condensation products of an alkaline oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol, for example, polyoxyethylene sorbitol monoleate, or condensation product of ethylene oxide with partial esters derived from fatty acids and hexitol and anhydrides, for example, polyoxyethelyne sobirtan monooleate, or water. The aqueous suspensions may also contain one or more suitable preservatives, for example, ethyl, or n-propyl, p-hydroxy benzoate, one or more suitable coloring agents, one or more suitable flavoring agents such as, cinnamon, chocolate, fruit flavors (i.e., cherry, grape, orange, strawberry, etc.), menthol, mints, vanilla and combination of two or more thereof, one or more suitable sweetening agents, such as calcium cyclamate, dextrose, fructose, galactose, glucose, glycerin, maltose, mannitol, mannose, ribose, partially hydrolyzed starch solids, partially hydrolyzed corn syrup solids, sodium cyclamate, sorbital, inulin, sucralose, sucrose, xylitol, or xylose, and one or more suitable coloring agents.

Dispersible powders and granules suitable for preparation of an aqueous suspension by the addition of water provide the active ingredient in admixture with a dispersing or wetting agent, suspending agent, and one or more preservatives. Suitable dispersing or wetting agents and suspending agents may be exemplified by those already mentioned above. Additional suitable excipients, for example, sweetening, flavoring, and coloring agents, may also be present.

Syrups and elixirs may be formulated with suitable sweetening agents, for example, one or more of glycerol, sorbitol, inulin, sucrose, or xylose. Such formulations may also contain suitable demulcents, preservatives such as citric acid, flavoring and coloring agents.

The individual compound of the pharmaceutical compositions may be administered alone or with other compositions, either substantially together or simultaneously, in separate or combined pharmaceutical formulations. By "substantially together", the active ingredients of the composition of the invention are administered to a patient in separate dosage forms, such that the active ingredients are administered either simultaneously or within a period of time, such that the patient receives benefit of the aggregate effects of the separate dosage forms. For example, the active ingredients may be taken together or within a few seconds to at least about 30 minutes of one another. Accordingly, methods of treatment of the present invention, therefore, include administration of the individual compounds of such combinations either substantially together or simultaneously in separate or combined pharmaceutical formulations. When administering or taking the active ingredients substantially together, but separately in the same or different dosage forms, the order in which they are administered or ingested is not critical.

Thus, according to a further aspect, the invention provides a method of treating nicotine withdrawal symptoms associated with smoking cessation, comprising administering to a patient in need thereof, a therapeutically effective amount of a medication comprising *Passiflora incarnata*. In one embodiment, a patient is treated by injecting the patient with the *Passiflora incarnata* medication of the present invention. In yet another embodiment the medication is administered orally.

In one embodiment, the medication is administered orally. The medication can be self administered and is given as a single dose or multiple doses over a period of weeks. The administration can continue until the nicotine product use has completely stopped and the appearance of symptoms has been alleviated. This will be different from person to person and will depend at least on the level of nicotine addiction, and to some extent, the personality of the individual taking the product. Typically, an effective therapeutic dose ranges from about 1.8 cc to about 3.0 cc. In other embodiments it is from 5 to 15 cc and in other embodiments it is over 15 cc as necessary to administer a therapeutically effective amount.

In another embodiment of the present invention, in place of an injection, the medication is administered transdermally via, for example, a scopolamine type patch, and/or orally, for example, via capsules or tablets according to accepted pharmacological principals While an administration is designed to obtain immediate and high levels of activity, a maintenance regime is designed to maintain lower levels of activity during the remainder of the withdrawal period. In another embodiment, the method of the present invention further comprises a step of continuing the effects of the medication administered via continued administration. Oral and transdermal agents, in addition to *Passiflora incarnate*, may be subsequently ingested by the patient to provide continued relief from craving and withdrawal symptoms of nicotine until the physiological effects of nicotine withdrawal are sufficiently minimized. Such non-limiting exemplary oral agents include nicotine patches. In an embodiment, the patient can begin taking the prescribed additional agent the day following receipt of the injected or otherwise administer *Passiflora incarnata* medication and continue for about two weeks, or until nicotine withdrawal symptoms are sufficiently minimized. While this method addresses the physiological aspects of nicotine withdrawal, there are, however, also psychological associations linked to smoking cigarettes which must be overcome for successful smoking cessation.

The invention provides in a further embodiment, a step for alleviating anxiety associated with nicotine withdrawal. Anxiolytic agents are prescribed using accepted pharmacological principals and subsequently ingested as prescribed by a patient. As used herein "anxiolytic agent" means any compound or composition having anxiolytic properties. Non-limiting examples of an anxiolytic include abecarnil, alpidem, benzodiazepines, buspirone, chlormezanone, chlorpromazine, clonidine, flupirilene, hydroxyzine, trandospirone, and meprobamate. In one embodiment, the patient begins taking the anxiolytic agent following receipt of the *Passiflora incarnata* medication. Alternatively, the anxiolytic agent can be administered simultaneously or substantially together with the *Passiflora incarnata* medication, for example, combined into and administered as a component of the *Passiflora incarnata* medication administered by the desired route.

The invention also provides in a further embodiment, a step for alleviating depression which can also be associated with nicotine withdrawal. Antidepressants are prescribed using accepted pharmacological principals and subsequently ingested as prescribed by a patient. In one embodiment, antidepressants such as serotonin reuptake inhibitors, bupropion, and buspirone are prescribed prior to or in conjunction with a patient's receipt of the *Passiflora incarnata* medication.

In a further embodiment, the invention also provides several methods of disassociating the habits of smoking by implementing a behavioral modification program and/or hypnosis or the like in combination with the *Passiflora incarnata* administration. These associations may be addressed prior to administration of the *Passiflora incarnata* medication in order to enhance the success of a smoking cessation program. Unfortunately, many patients resume smoking well after the physiological addiction has resolved. Usually this is due to poor coping habits and lack of support. Therefore, smoking cessation success rates may also be enhanced by routine support and counseling after the physiologic withdrawal has resolved. Non-limiting examples of the formats in which smoking cessation support and counseling is offered include, telephone conference calls, internet discussion boards, internet chat rooms, group meetings and individualized counseling sessions. Counseling and support may also be provided to a patient through various media, such as video tapes, CDs, DVDs and audiotapes having recorded thereon various educational and support materials for the cessation of smoking.

In order to further illustrate the present invention and the advantages thereof, the following specific non-limiting examples are given, it being understood that these examples are intended only to be illustrations of the effectiveness of the present invention without serving as a limitation on the scope of the present invention in the treatment of smoking cessation withdrawal symptoms.

EXAMPLES

Drug Treatment of Rats

Male Wistar rats (Charles River, Raleigh, N.C.) were provided with food and water ad libitum on a 12 hour light/dark cycle for 2-3 weeks before beginning any treatments. For all experiments, rats were approximately 45-65 days old and weighed between 148 and 195 g at the beginning of an experiment. Injections of nicotine or its vehicle (water) were subcutaneous (s.c.) administered at 0.4 mg/kg nicotine (Sigma Aldrich, St. Louis, Mo.) and 2 ml/kg. Injections of aqueous passion flower extract (Nature's Answer, Hauppage, N.Y.) or vehicle (1:1 glycerin:water) were intraperitoneal (i.p.) administered at 800 mg/kg and 0.16 ml/kg.

Assessment of Time to Habituation and of Acute Nicotine on Spontaneous Activity

Drug-naive rats were placed individually in an open field for determination of spontaneous activity using the Limelight video tracking system (ActiMetrics, Wilmette, Ill.). Each rat was monitored in the open field for 30 minutes to determine the time course of habituation. Immediately afterward, each rat was injected with vehicle that was subsequently used for nicotine injection at 2 ml/kg and the rats were monitored for 50 minutes. Then each rat was removed from the chamber briefly to be injected s.c. with 0.4 mg/kg nicotine and monitored for another 90 minutes.

Assessment of the Effect of Passion Flower Extract on Nicotine Sensitization

To produce nicotine sensitization, rats were injected once/day for 4 consecutive days with either nicotine or vehicle. On day 5, known as the test day, rats were divided into four groups; half of those that had received vehicle on days 1-4 were pre-treated with passion flower extract (vehicle-passion flower group) and the other half with vehicle (vehicle-vehicle group). Analogously, half of the rats that received nicotine on days 1-4 received a pre-treatment of i.p. 1:1 water:glycerin (nicotine-vehicle group) on day 5, while the other half was given a pre-treatment of i.p. passion flower extract (nicotine-passionflower group). Each rat was monitored in the open field for 100 consecutive minutes, starting approximately 23 hours after the day 4 nicotine treatment. Before any injections on day 5, rats were placed in the activity chambers until an injection of passion flower extract or vehicle at 25 minutes, then monitored for another 25 minutes, at which point all rats received an injection of nicotine and were monitored for 50 additional minutes.

Data Analysis

Mean velocity (in cm/s) over each 1 sec period was extracted using the LimeLight software and that data was used to calculate the average and SEM of the mean velocities for each 5 minute interval for each treatment group. Figures show the time at the end of the 5 minute period (e.g., 10 minutes is the 5-10 minute interval). In the preliminary assay of nicotine versus vehicle, there were 6 rats and in the chronic nicotine study there were 8-10 rats in each group.

Results

In the first assays, the length of time that it took the rats to habituate to the spontaneous activity chambers and the time course of the effects of a single dose of nicotine on spontaneous activity was determined. Drug-naïve rats were placed in the open field chambers and their activity recorded until their spontaneous activity had largely subsided. The amount of spontaneous activity in the first 5 minutes was high, 3.5 cm/s average velocity, and decreased to low levels, 0.5 cm/s, during the 25-30 minute interval (FIG. 1). Next, each rat was given a s.c. injection of vehicle and immediately returned to the open field chamber for another 50 minutes. It was noted that the spontaneous activity was initially higher than at the end of the habituation period, 1.5-1.7 cm/s, but not as high as when first introduced to the chamber. Again, it took about 25 minutes for the level of spontaneous activity to decrease to between 0.5 and 0.7 cm/s where it remained for the rest of the session. At the end of this 50 minute period, rats were injected s.c. with 0.4 mg/kg nicotine and again returned to the chambers for another 90 minutes (FIG. 1). While the amount of spontaneous activity initially rose from the first to the second 5-minute interval, from that point it generally declined from 2.5 cm/s to 0.8 cm/s over the first 60 minutes. During the last 30 minutes, the level of spontaneous activity remained low at between 0.6 and 0.1 cm/s. The amount of spontaneous activity was initially similar to, and not significantly different from, that seen in the vehicle-treatment phase. Activity after nicotine treatment peaked from 5-15 minutes after injection (intervals of 5-10 and 10-15 minutes), and was significantly different from vehicle treatment in the intervals between 10 and 35 minutes after injections (with the exception of the interval from 15-20 minutes) by 2-way ANOVA (treatment $p<0.0001$) followed by Bonferroni's posttest at $p<0.05$. After nicotine treatment, rats moved between 2.5 and 1.4 cm/s (an average of $1.9\pm0.2$ cm/s) during the 10-35 minute intervals, while during the same period after vehicle treatment the values were between 1.3 and 0.3 cm/s (an average of $0.8\pm0.1$ cm/s).

Figure 2:
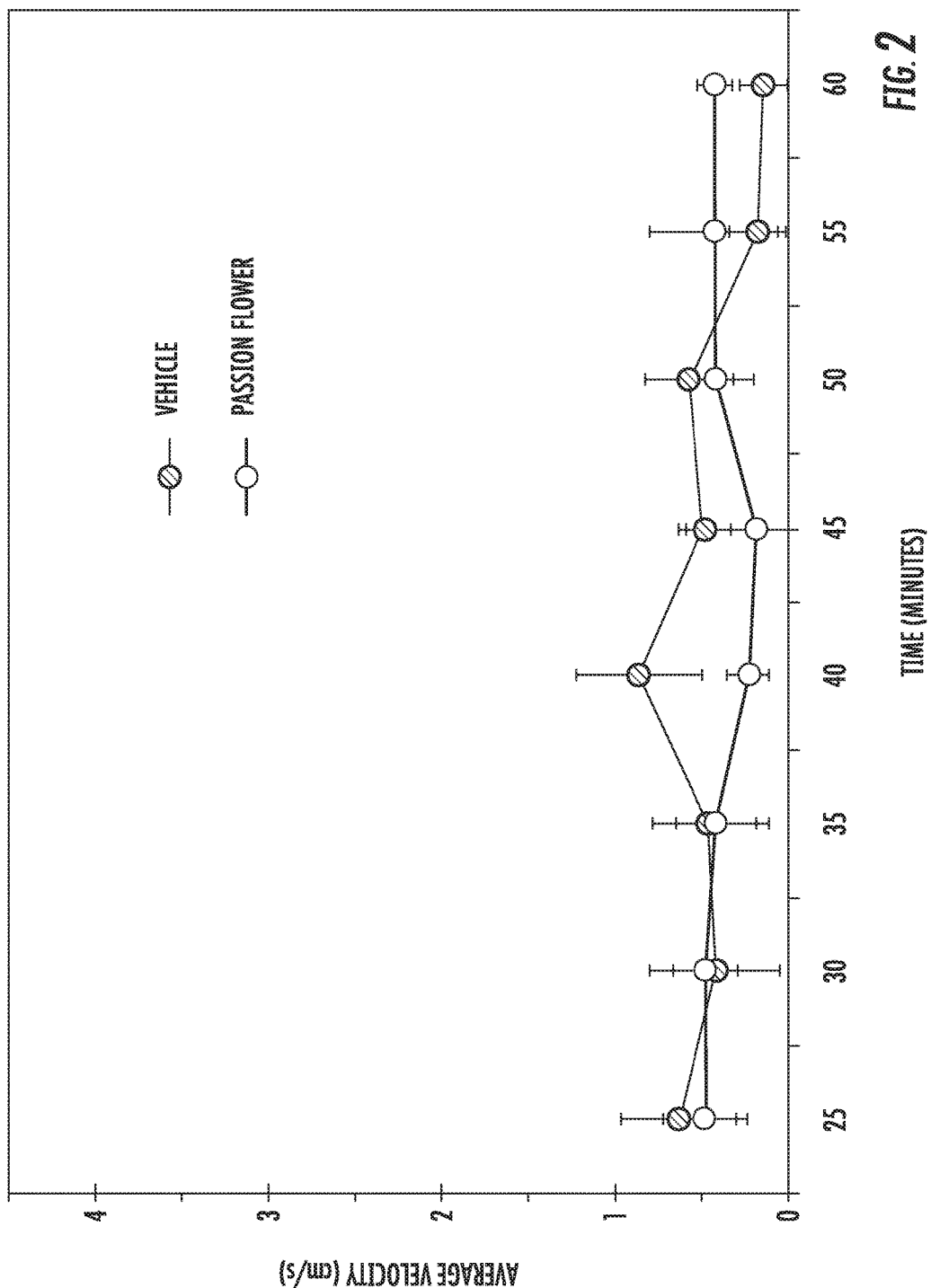
Figure 3:
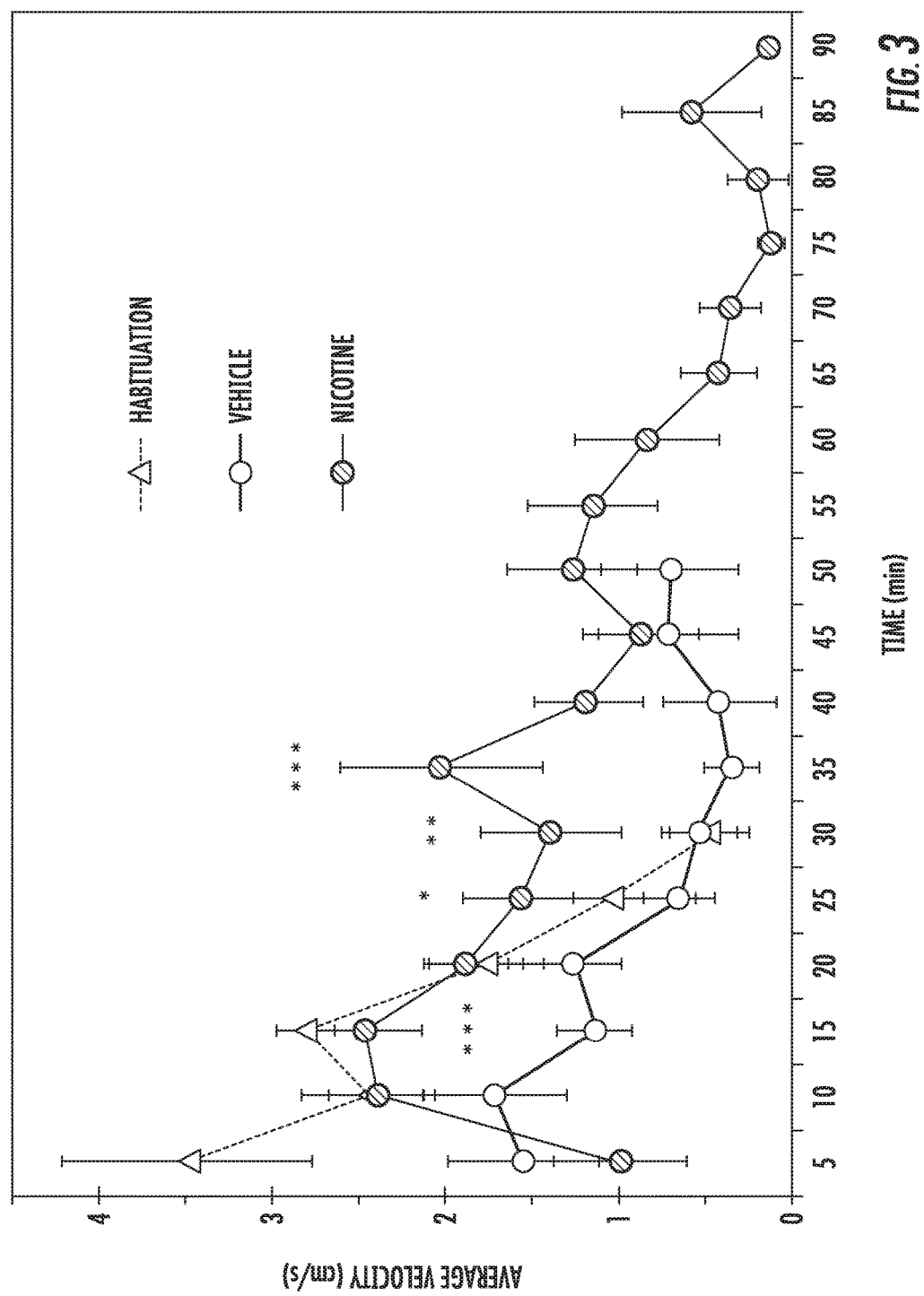

Once the habituation period and time to the peak effect of a dose of nicotine was determined, the nicotine sensitization experiments began. In these experiments, rats were sensitized to nicotine by the administration of 0.4 mg/kg s.c. nicotine or vehicle (as a control) on days 1-4, and the testing was done on day 5. Similar to the preliminary study above, the rats began at a high level of spontaneous activity of approximately 3.5 cm/s then habituated to the open field chambers (FIG. 2). At the last measurement during the habituation phase taken at 15-20 minutes, the activity for the four groups averaged $1.4\pm0.1$ cm/s (FIG. 1). Passion flower extract or its vehicle was administered i.p. between 20 and 25 minutes and activity was assessed while allowing time for the extract to be absorbed. The activity of all groups remained low during this period with an average of $0.32\pm0.03$ cm/s from 25-45 minutes (FIG. 2). Between 45 and 50 minutes, nicotine was injected s.c. into all rats. Activity increased and peaked in all four groups at 60-65 minutes (FIG. 2). By 65-70 minutes the nicotine-vehicle group exhibited significantly greater activity than the other three, and this difference persisted up to the 90 minute time point (except that the difference at 75-80 minutes was not statistically significant). Significance was determined by 2-way ANOVA where the effect of treatment was $p<0.0001$. To determine differences between groups at specific time points, one-way ANOVAs comparing all four groups were performed at each time interval. In each case where a difference was noted above, the nicotine-vehicle group had significantly greater activity from the other three, while none of the other groups were different from each other.

This experiment determined that the passion flower extract could antagonize the expression of motor sensitization by nicotine. Following the daily nicotine treatments that produced sensitization, the challenge dose of nicotine on the test day caused an increase in locomotion above what was seen after an acute or first dose of nicotine. There are two ways in which pharmacotherapies for nicotine addiction are tested in motor sensitization models. One is known as antagonism of motor sensitization, and involves giving the test compound concurrent with nicotine during the induction of dependence, but not on the day of the challenge dose of nicotine. The other is known as antagonism of the expression of motor sensitization, and involves giving the test compound only once shortly before the administration of the challenge dose of nicotine. If a test drug treatment blocks the increased response to the challenge dose of nicotine in this model, it indicates decreases in the signs of nicotine withdrawal. In these studies, the nicotine-vehicle and nicotine-passion flower groups were the nicotine-sensitized groups in which motor sensitization should have been induced. The nicotine-vehicle group (control nicotine sensitized group) showed significantly greater activity than the vehicle-vehicle group following the challenge dose of nicotine, reflecting nicotine sensitization. Comparison of the nicotine-vehicle and nicotine-passionflower groups illustrates that passion flower extract antagonized the expression of motor sensitization, since the nicotine-passion flower group showed the same level of activity as the non-sensitized vehicle-vehicle control group following nicotine challenge.

REFERENCES

Akhondzadeh S, Kashani L, Mobaseri M, Hosseini S H, Nikzad S, Khani M (2001a) Passionflower in the treatment of opiates withdrawal: a double-blind randomized controlled trial. Journal of clinical pharmacy and therapeutics 26:369-373.

Akhondzadeh S, Naghavi H R, Vazirian M, Shayeganpour A, Rashidi H, Khani M (2001 b) Passion flower in the treatment of generalized anxiety: a pilot double-blind randomized controlled trial with oxazepram. Journal of clinical pharmacy and therapeutics 26:363-367.

Benowitz N L (1996) Pharmacology of nicotine: addiction and therapeutics. Annual review of pharmacology and toxicology 36:597-613.

Dani J A, De Biasi M (2001) Cellular mechanisms of nicotine addiction. Pharmacology, biochemistry, and behavior 70:439-446.

Dhawan K (2003) Drug/substance reversal effects of a novel tri-substituted benzoflavone moiety (BZF) isolated from *Passiflora incarnata* Linn.—a brief perspective. Addiction biology 8:379-386.

Kalivas P W, Churchill L, Klitenick Mass. (1993) GABA and enkephalin projection from the nucleus accumbens and ventral pallidum to the ventral tegmental area. Neuroscience 57:1047-1060.

Kayir H, Goktalay G, Yildirim M, Uzbay T I (2009) Clozapine inhibits development and expression of nicotine-induced locomotor sensitization in rats. Synapse (New York, N.Y. 63: 15-21.

Krenn L (2002) [Passion Flower (*Passiflora incarnata* L.)—a reliable herbal sedative]. Wiener medizinische Wochenschrift (1946) 152:404-406.

Mansvelder H D, McGehee D S (2002) Cellular and synaptic mechanisms of nicotine addiction. Journal of neurobiology 53:606-617.

Movafegh A, Alizadeh R, Hajimohamadi F, Esfehani F, Nejatfar M (2008) Preoperative oral *Passiflora incarnata* reduces anxiety in ambulatory surgery patients: a double-blind, placebo-controlled study. Anesthesia and analgesia 106:1728-1732.

Nassiri-Asl M, Shariati-Rad S, Zamansoltani F (2007) Anticonvulsant effects of aerial parts of *Passiflora incarnata* extract in mice: involvement of benzodiazepine and opioid receptors. BMC complementary and alternative medicine 7:26. Centers for Disease Control and Prevention (CDC) (2008) Cigarette smoking among adult—United States, 2007. In: *Mmwr*. pp 1221-1226.

Soulimani R, Younos C, Jarmouni S, Bousta D, Misslin R, Mortier F (1997) Behavioral effects of *Passiflora incarnata* L. and its indole alkaloid and flavonoid derivatives and maltol in the mouse. Journal of ethnopharmacology 57:11-20.

Werneke U, Turner T, Priebe S (2006) Complementary medicines in psychiatry: review of effectiveness and safety. Br J Psychiatry 188:109-121.

Zanoli P, Avallone R, Baraldi M (2000) Behavioral characterization of the flavonoids apigenin and chrysin. Fitoterapia 71 Suppl 1:S117-123.

What is claimed is:

1. A method for treatment of depression associated with nicotine product use cessation in a patient in need thereof consisting of administering to the patient a plant composition, the plant composition consisting of a water extract of *Passiflora incarnata* and a non-plant anti-depressant.

* * * * *